United States Patent
Brand

(10) Patent No.: US 10,406,104 B2
(45) Date of Patent: Sep. 10, 2019

(54) NANOSUSPENSION CONTAINING PARTICLES AND EXTRACT OF NATURAL MATERIALS

(71) Applicant: Apurano Life Sciences GmbH, Warngau (DE)

(72) Inventor: Werner Brand, Warngau (DE)

(73) Assignee: Apurano Life Sciences GmbH, Warngau (DE)

(*) Notice: Subject to any disclaimer, the term of this patent is extended or adjusted under 35 U.S.C. 154(b) by 0 days.

(21) Appl. No.: 15/749,877

(22) PCT Filed: Aug. 4, 2016

(86) PCT No.: PCT/EP2016/068644
§ 371 (c)(1),
(2) Date: Feb. 2, 2018

(87) PCT Pub. No.: WO2017/021491
PCT Pub. Date: Feb. 9, 2017

(65) Prior Publication Data
US 2018/0221283 A1    Aug. 9, 2018

(30) Foreign Application Priority Data

Aug. 4, 2015 (EP) ..................................... 15179748

(51) Int. Cl.
*A61K 9/19* (2006.01)
*A61K 36/9066* (2006.01)
(Continued)

(52) U.S. Cl.
CPC .............. *A61K 9/19* (2013.01); *A23L 33/105* (2016.08); *A61K 9/10* (2013.01); *A61K 9/1075* (2013.01);
(Continued)

(58) Field of Classification Search
CPC .... A61K 9/19; A61K 9/1075; A61K 36/9066; A23L 33/105
See application file for complete search history.

(56) References Cited

U.S. PATENT DOCUMENTS 10,213,382 B2 * 2/2019 Brand ................... A61K 9/10
2012/0195949 A1   8/2012 Miuchi et al.
(Continued)

FOREIGN PATENT DOCUMENTS

CN       1416846 A    11/2003
CN       1824255 A    8/2006
(Continued)

OTHER PUBLICATIONS

European Pharmacopoeia 5.0; 4.1.3. Buffer Solutions; pp. 430-435.
(Continued)

*Primary Examiner* — Carlos A Azpuru
(74) *Attorney, Agent, or Firm* — Grüneberg and Myers PLLC

(57) ABSTRACT

The present application relates to a method for the preparation of a nanosuspension comprising nanoparticles of at least one natural material and an extract of at least one natural material, wherein the method comprises the steps of providing particles of at least one natural material having a particle size ($D_{100}$) of less than 320 μm; providing an extract of at least one natural material; dispersing said particles of at least one natural material and said extract of at least one natural material in a solvent; and milling the dispersion to a particle size ($D_{90}$) of below 1000 nm ($D_{90}$<1000 nm). Furthermore, the present application also relates to a nanosuspension prepared according to said method, and the use of such nanosuspension for the preparation of a medicament and/or nutritional supplement.

19 Claims, 3 Drawing Sheets

(51) Int. Cl.
  *A61K 47/24* (2006.01)
  *A61K 9/10* (2006.01)
  *A61K 9/107* (2006.01)
  *A61K 9/14* (2006.01)
  *A61K 31/12* (2006.01)
  *A23L 33/105* (2016.01)
  *A61K 9/51* (2006.01)

(52) U.S. Cl.
  CPC .............. *A61K 9/148* (2013.01); *A61K 31/12* (2013.01); *A61K 36/9066* (2013.01); *A61K 47/24* (2013.01); *A23V 2002/00* (2013.01); *A61K 9/145* (2013.01); *A61K 9/5176* (2013.01)

(56) References Cited

U.S. PATENT DOCUMENTS

| | | | |
|---|---|---|---|
| 2012/0244134 A1* | 9/2012 | Chen | A23L 29/10 424/94.1 |
| 2015/0147359 A1 | 5/2015 | Egberg et al. | |
| 2016/0346201 A1 | 12/2016 | Brand | |

FOREIGN PATENT DOCUMENTS

| | | |
|---|---|---|
| CN | 1883685 A | 12/2006 |
| CN | 101757035 A | 6/2010 |
| EP | 2 848 243 A1 | 3/2015 |
| WO | 2015/081018 | 6/2015 |
| WO | WO 2015/114164 A1 | 8/2015 |

OTHER PUBLICATIONS

European Pharmacopoeia 5.0; Extracts; pp. 570-572.
"Plurol Oleique" National Center for Biotechnology Information, U.S. National Library of Medicine ([retrieved from on-line website: https://pubchem.ncbi.nlm.nih.gov/compound/9963243 last visit May 29, 2017).
"Gelucire® 44/14: Lauroyl polyoxyl-32 glycerides NF from Gattefossé" American Pharmaceutical Review ([retrieved from on-line website: http://www.americanpharmaceuticalreview.com/25260-Excipients/9506442-Gelucire-44-14-Lauroyl-polyoxyl-32-glycerides-NF/ last visit May 29, 2017).
"Labrafil® M1944 CS: Oleoyl polyoxyl-6 glycerides NF from Gattefossé" American Pharmaceutical Review ([retrieved from on-line website: http://www.americanpharmaceuticalreview.com/25260-Excipients/9506443-Labrafil-M1944-CS-Oleoyl-polyoxyl-6-glycerides-NF/ last visit May 29, 2017).
"Labrasol® Caprylocaproyl polyoxyl-8 glycerides NF from Gattefossé" American Pharmaceutical Review ([retrieved from on-line website: http://www.americanpharmaceuticalreview.com/25260-Excipients/7682699-Labrasol/ last visit May 29, 2017).
Tayyem et al., "Curcumin content of turmeric and curry powders," *Nutr. Cancer* 2006, 55(2), 126-31 (abstract).

* cited by examiner

US 10,406,104 B2

NANOSUSPENSION CONTAINING PARTICLES AND EXTRACT OF NATURAL MATERIALS

BACKGROUND OF THE INVENTION

Field of the Invention

The present application relates to a method for the preparation of a nanosuspension comprising nanoparticles of at least one natural material and an extract of at least one natural material, a nanosuspension prepared according to said method, and the use of such nanosuspension for the preparation of a medicament and/or nutritional supplement.

Background of the Invention

Natural materials, such as plants, cyanobacteria, algae or fungi, contain active agents which have the potency for treating diseases. In order to elute these active agents from natural materials, a variety of pharmaceutical preparations are known including aqueous or alcoholic percolation or maceration, dried powder extracts in form of tablets or capsules, or injectable dosage formulations. However, there are many disadvantages associated with these types of administration. Many of the ingredients are degraded within the gastrointestinal tract or undergo first-pass metabolism in the liver. In addition, parts of the population experience difficulty swallowing pills or are unable to tolerate any solids. Furthermore, many active agents of natural materials are poorly water soluble. The potency and therapeutic effects of many active agents of natural materials are therefore limited.

Diseases are often triggered by biochemical processes in human organism. Many of these processes are regulated by enzymes like e.g. the inflammatory pathway. Pharmaceutically active agents can affect these enzymes for therapeutic use while their inhibition or activation depends on the potency of an antagonist or agonist agents. With a minor potency of the active agent the concentration has to be increased to enhance its effect. Hence, increasing the effective concentration of an active agent in a pharmaceutical preparation is a constant aim.

However, the prior art methods for preparing a nanosuspension lack a method for the preparation of a nanosuspension from natural materials which may serve all needs. There is thus still a need for methods for preparing a nanosuspension from natural materials, which nanosuspension may be advantageously used in the treatment or prevention of diseases.

SUMMARY OF THE INVENTION

It is thus one object of the present disclosure to provide a method for the preparation of a nanosuspension from the whole or parts of natural materials combined with an extract of natural material having a high amount of natural material, i.e., a high concentration of natural material, in particular of active agent.

In a first aspect, the present disclosure provides a method for the preparation of a nanosuspension as disclosed in claim 1.

In another aspect, the present disclosure provides a nanosuspension obtainable according to a method of the first aspect.

In another aspect, the present disclosure provides a nanosuspension according to the first aspect for use in the preparation of a medicament for buccal, topical or oral application to an animal, preferably a human, or for use in the preparation of a medicament for parenteral, intrathecal, intravenous, transdermal, or trans-mucosal application, preferably buccal, topical or oral application, to an animal, preferably a human.

In another aspect, the present disclosure provides a nanosuspension according to the first aspect for use in the treatment or prevention of cancer, inflammatory bowel disease (IBD), arthritis, human immunodeficiency virus (HIV), other viral diseases, dermatological diseases, such as neurodermatitis or psoriasis, or auto-immune diseases, such as multiple sclerosis.

In still another aspect, the present disclosure provides the use of a nanosuspension according to the first aspect for the preparation of a medicament.

DETAILED DESCRIPTION OF THE INVENTION

Figure 1:
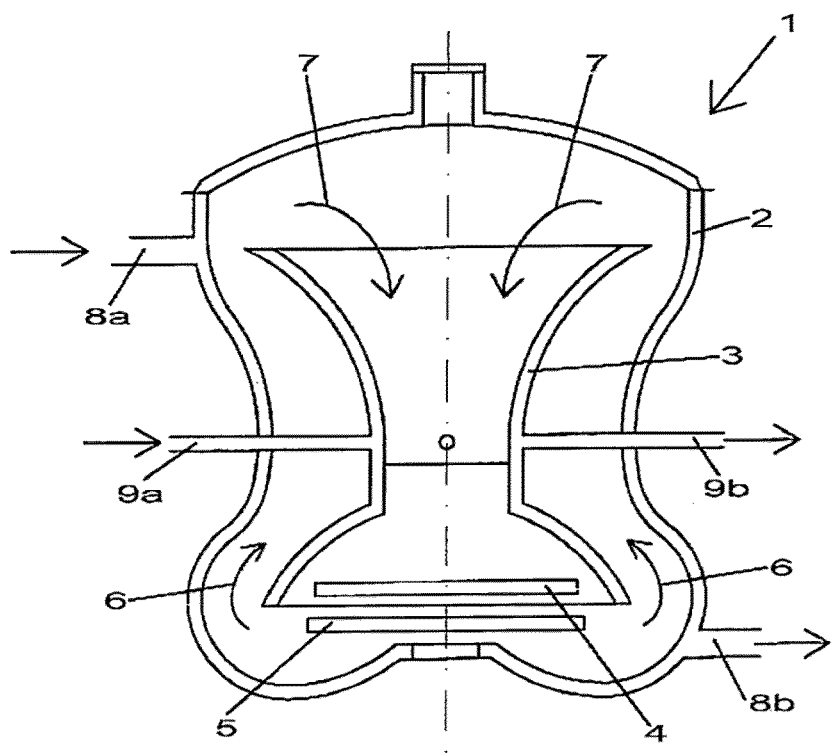
FIG. 1 shows the schematic drawing of a colloidator.

The present disclosure relates to a method for the preparation of a nanosuspension comprising nanoparticles of at least one natural material and an extract of at least one natural material, wherein the method comprises the steps of a1. Providing particles of at least one natural material having a particle size ($D_{100}$) of less than 320 µm;

a2. Providing an extract of at least one natural material;

b. Dispersing said particles of at least one natural material of step a1. and said extract of at least one natural material of step a2. in a solvent;

c. Milling the dispersion of step b. to a particle size ($D_{90}$) of below 1000 nm ($D_{90}$<1000 nm); and d. Adding a stabilizer.

Without being bound by any theory, it is believed that the specific combination of natural materials in nanoparticulate form and an extract of a natural material increases the efficacy of both, i.e., a synergistic effect is present. On the one hand, by addition of an extract, the effective concentration of an active agent may be increased. On the other hand, with the presence of the natural material, potentially healthy additives are supplied by the (entire) natural material to support the effect of the active agents, such as the resorption or the stability of the active agent. In addition thereto, the solubility in pharmaceutically acceptable solvents, such as water and/or ethanol, may be increased by the use of nanoparticulate matter, as prepared according to the methods disclosed herein. Furthermore, the nanoparticles of the nanosuspension of the present disclosure, when applied as a medicament, are believed to be taken up faster and to a higher amount compared to other preparations. Finally, also the availability of the active agent contained in the natural material is increased by the method disclosed herein.

The present invention as illustratively described in the following may suitably be practiced in the absence of any element or elements, limitation or limitations not specifically disclosed herein. The present invention will be described with respect to particular embodiments and with reference to certain figures but the invention is not limited thereto but only by the claims. Terms as set forth hereinafter are generally to be understood in their common sense unless indicated otherwise.

Definitions

Where the term "comprising" is used in the present description and claims, it does not exclude other elements. For the purposes of the present invention, the term "consisting of" is considered to be a preferred embodiment of the term "comprising". If hereinafter a group is defined to comprise at least a certain number of embodiments, this is also to be understood to disclose a group, which preferably consists only of these embodiments.

Where an indefinite or definite article is used when referring to a singular noun, e.g. "a", "an" or "the", this includes a plural of that noun unless specifically stated otherwise.

Terms like "obtainable" or "definable" and "obtained" or "defined" are used interchangeably. This, e.g., means that, unless the context clearly dictates otherwise, the term "obtained" does not mean to indicate that e.g. an embodiment must be obtained by e.g. the sequence of steps following the term "obtained" even though such a limited understanding is always included by the terms "obtained" or "defined" as a preferred embodiment.

A "nanosuspension" as used herein refers to a suspension of nanoparticles in a solvent, such as, for example, water, ethanol, or a mixture thereof. The nanosuspension may additionally comprise stabilizing agents, or other compounds. A nanosuspension comprises a poorly or non-water-soluble compound in the form of nanoparticles suspended in a solvent. Such nanosuspension is used to enhance the "solubility" (or dispersibility) of a compound that is poorly or not soluble in a solvent (such as water or ethanol), a lipid media, or both. As a result of increased "solubility", a higher plasma blood level of the poorly soluble compound is reached and the maximum plasma blood level of said compound may be reached faster.

The term "particles of at least one natural material" as used herein refers to particles of one natural material, or a mixture of particles of more than one natural material. When referring to particles of one natural material, different parts or the whole of the natural material may be used. Similarly, when referring to particles of more than one natural material, also different parts of the different natural materials may be used. The term "particles of at least one natural material" may also be referred to as "particles" in the following.

"Nanoparticles" as used herein are particles having a particle size of below 1000 nm. The compound nanoparticles in the solvent may be primary particles, or agglomerated particles composed of smaller particles. The particle size in the nanosuspension may be measured with a laser diffraction analyzer (e.g. Beckman Coulter LS 13320 or Horiba LA-950).

The term "solubility" or "solubility limit" of a natural material as used in the present disclosure relates to the maximum amount of natural material that may be dissolved in a solvent. For the purposes of the present disclosure, the solubility of a natural material in a specific solvent may be determined as follows: an initial amount of dry natural material with a particle size $D_{100} < 320$ µm is used to prepare a suspension of said natural material in a solvent, such as distilled water, at a concentration of 5% or 10% (w/w). For the preparation of said suspension, the natural material is suspended for 60 minutes in a solvent at a temperature of 30° C. The resulting suspension is then centrifuged at 1500 g for 30 minutes, and precipitates are separated from supernatant and weighed for control reasons. The supernatant is dried at 60° C. for 24 h, resulting in the natural material dissolved in the supernatant (dry basis), and weighed. The solubility is calculated using the following equation:

Solubility (%)=mass of supernatant (dry basis)×100/ mass of initial natural material powder (dry basis).

The term "solubility factor" as used in the present disclosure relates to the amount of a natural material in a nanosuspension according to the present disclosure in relation to the solubility or solubility limit of said natural material in the solvent used to prepare the nanosuspension. The solubility factor is the total amount of natural material present in the nanosuspension (in % (w/w)) divided by the solubility of said natural material in the solvent used. In other words, if a solubility factor of 1 is given, the solubility limit of the natural material in said solvent is reached. At a solubility factor below 1, the amount of natural material in the nanosuspension is below the solubility limit, and a solubility factor of above 1 indicates that more than the amount of natural material soluble in said solvent is present in the nanosuspension, i.e., the concentration of the natural material in the nanosuspension is above its solubility limit.

The "total amount of natural material" contained in the nanosuspension refers to the amount of dry mass, i.e., the mass of dry natural material without any solvent or stabilizer. The dry mass of the nanosuspension is thus the sum of the dry mass of the particles of at least one natural material and the extract of at least one natural material. This is also referred to as the solid matter of the nanosuspension. The water content of the dry material is below 8% (w<8%), preferably below 5% (w<5%), further preferably 2% (w<2%).

The term "cellulose fiber" as used in the present disclosure relates to a plant fiber (especially wood fiber) consisting of a polysaccharide with a linear chain of several hundred to over ten thousand β-1,4-D-glucose units with a length of the fiber of >1 µm. Cellulose fibers therefore do not consist of β-1,3/1,6-glucan with a geometrical shape of a sphere with a diameter <1 µm or an ellipsoid with semi axis length <1 µm.

The term "extract of at least one natural material" refers to an extract of one natural material, or an extract of more than one natural material. The latter is used herein as referring to the extract of more than one natural material prepared by the simultaneous extraction of more than one natural material, or as a mixture or combination of more than one extract of a natural material, i.e., a combination or mixture of several extracts of one natural material each. The term "extract of at least one natural material" may also be referred to as "extract" in the following.

The term "extract" is defined as described in the European Pharmacopoeia 5.0 (publisher: Council of Europe, 5$^{th}$ edition, July 2004, ISBN 9287152810), pages 570 to 572, which are incorporated herein by reference. As such, a liquid extract is prepared by using ethanol of suitable concentration or water to extract the natural material, such as a herbal drug. In the same context, a dry extract is a solid preparation obtained by evaporation of the solvent used for the preparation of the liquid extract. Dry extracts usually have a loss on drying or a water content of not greater than 5 per cent (m/m).

The Extract of Natural Material

According to the present disclosure, the composition comprises an extract of at least one natural material. Especially preferred are aqueous extracts. It is understood that the concentration of active ingredients of the extracts of natural materials, such as plants and algae, highly depend on the source of the natural products and the amount of extraction medium. The preferred extraction medium according to the present disclosure is distilled water. The extract of the at least one natural material may be prepared from a part or the whole of said natural material, preferably the whole of said natural material. The method of the present disclosure may be used for any natural material as a whole, or parts thereof. As an example, only parts of a plant may be used, such as the roots, seeds, stems, leaves, fruits, flowers, or the like, depending on the type of natural material.

The natural material may be extracted using water, preferably distilled water, at a temperature in the range of 20 to 60° C., preferably 25 to 50° C. The water may be poured over the natural material in dried or fresh (i.e., non-dried) form, then allowed to brew or extract for an appropriate time, such as 1 minute to 72 hour, preferably 5 minutes to 120 minutes. Finally, the extracted natural material are filtered or centrifuged off to result in a filtrate containing extracts of the natural material.

Alternatively, commercially available extracts of the corresponding natural material may be used in accordance with the present disclosure.

In a preferred embodiment, the natural material of the present disclosure are extracted with aqueous extraction media, preferably water, more preferably distilled water, resulting in an aqueous extract of the natural material, such as plant or algae. However, also other extraction media may be used. Examples of other extraction media include, but are not limited to organic solvents, such as alcohols, preferably methanol, ethanol and propanol, acetic acid, acetic acid esters, acetyl acetone, and mixtures thereof, as well as mixtures with water. Particularly preferred extraction media include water and ethanol.

The extract may be added in liquid or dry form in step b., and prior to step c. Usually, the extract of a natural material also contains particles of said natural material. The particles in the extract are smaller in size, but still have a particle size ($D_{100}$) of below about 100 µm, or below 50 µm. If the extract is added prior to the milling step c., also the particles contained in the extract are reduced in size, resulting in a nanosuspension having a particle size ($D_{90}$) of below 1000 nm (i.e., below 1 µm).

In another preferred embodiment, the extract of at least one natural material is dried in a step a1.1, prior to step a1., preferably lyophilized (freeze-dried) and/or thermally dried. The dry powder of the extract may then be added in step b.

In another preferred embodiment, the extract of the natural material as used in the preparation of the nanosuspension and provided in step a2. can be an extract according to the definition of the European Pharmacopoeia (as referred to above) with a concentration of the active agents of more than 20%, preferable more than 30%, more preferable more than 50%.

In another preferred embodiment, the extract of at least one natural material is selected from a dry powder, a soft extract, and a liquid extract, and preferably selected from a dry powder, an aqueous extract, and an alcoholic (ethanolic) extract.

The Particles of Natural Material

In the method according to the present disclosure, particles of at least one natural material are provided in step a1.

For the preparation of the nanosuspension of the present disclosure, parts or the whole of at least one natural material is used. The natural material is provided in step a1. in form of particles having a particle size ($D_{100}$) of below 320 µm. The natural material, i.e., the particles, may be provided in dry form, in fresh form (i.e., as present in the nature), or containing a specific water content. The powder or particles of natural material may be added in any of the indicated forms in step b. together with the extract to a solvent.

In another preferred embodiment, the natural material as used in the preparation of the nanosuspension is dried in a step a1.1, prior to step a1., preferably lyophilized (freeze-dried) and/or thermally dried.

The particles of the natural material as used for the preparation of the nanosuspension preferably have a low water content. The term "water content" or "residual moisture" as used in the present disclosure refers to the water content w of the material, such as the natural material, calculated from the mass of the moist or wet material $m_{wet}$ and the mass of the dry material without water $m_{dry}$ and the mass of the material with a residual moisture $m_{res}$ by use of the following formula: residual moisture content [%] $w=(m_{res}-m_{dry})/(m_{wet}-m_{dry})*100\%$ In another preferred embodiment, the natural material as used in the preparation of the nanosuspension and provided in step a1. of the method as disclosed above has a water content w of below 15% (w<15%), preferably below 12% (w<12%), more preferably below 10% (w<10%), and most preferably below 8% (w<8%).

Such low water content may be advantageous when preparing the nanosuspension. In addition, it may be helpful when bringing the natural material to a particle size ($D_{100}$) of less than 320 µm. There are different methods known in the art to reduce the water content of a natural material, and any of these methods may be used in combination with the present disclosure. As an example, the natural material may be lyophilized (i.e., freeze-dried) or thermally dried. It may be advantageous to clean, peal and/or core the natural materials, depending on the type of natural material prior to the drying step. In the following, two exemplary methods for drying are given.

Natural materials can be lyophilized with a lyophilizer, e.g., in a four-step process as follows:

- The natural material is cut into smaller pieces of about 1-2 cm with a knife depending on the size and structure of the natural material;
- The 1-2 cm pieces are put in a knife mill (e.g. Grindomix® 200 or 300 from Retsch GmbH, Germany) and ground with the following parameters: 10 sec at 2000 rpm following 10 sec at 5000 rpm and terminal 20 sec at 10.000 rpm;
- The resulting pulp is frozen at −18° C. for 4 h and further put into a lyophilizer and lyophilized until the product temperature is 20° C.

It is understood that the above freeze drying process is exemplary, and a person skilled in the art may adapt the process, depending on the type of the natural material. As an example, cyanobacteria may be directly freeze-dried, without prior grinding or cutting. Similarly, also the parameters for cutting the pieces in a knife mill may be adjusted according to the needs.

Natural materials can be also dried on air or in an oven at a temperature of, e.g., 36-45° C. until the residual moisture content is as low as 8%, depending on the thermal sensitivity of the compounds in the natural material.

In another preferred embodiment, the natural material as used in the preparation of the nanosuspension and provided in step a. of the method as disclosed above is pre-ground prior to and/or after the drying in a step a.1, preferably in a knife mill, and optionally sieved to a particle size ($D_{100}$) of less than 320 µm. Such grinding of the natural material may be done with the natural material as it is, i.e., without prior cutting or drying, or the natural material may be cut into pieces and/or dried as described above. Additionally, the natural material may be sieved in order to provide a powder of natural material having a particle size ($D_{100}$) of less than 320 µm.

An exemplary method for pre-grinding and sieving of a freeze-dried natural material may be as follows:

The freeze-dried course natural material powder is put in a knife mill (e.g. Grindomix® 200 or 300 from Retsch GmbH, Germany) and ground with the following parameters: 10 sec at 2000 rpm following 10 sec at 5000 rpm and terminal 20 sec at 10.000 rpm;

The course natural material powder from the knife mill process is sieved with a sieve of a mesh size of 320 µm;

The natural material particles larger than 320 µm are again put in the knife mill for further grinding and following sieving with the 320 µm sieve. The residual of the second or third grinding step may be discarded.

Similarly, an exemplary method for pre-grinding and sieving of a thermally dried natural material may be as follows:

The thermally dried natural material is cut into smaller pieces of about 1-2 cm with a knife;

The 1-2 cm pieces are put in a knife mill (e.g. Grindomix® 200 or 300 from Retsch GmbH, Germany) and ground with the following parameters: 10 sec at 2000 rpm following 10 sec at 5000 rpm and terminal 20 sec at 10.000 rpm;

The course natural material powder from the knife mill process is sieved with a sieve of a mesh size of 320 µm;

The natural material particles larger than 320 µm are again put in the knife mill for further grinding and following sieving with the 320 µm sieve. The residual of the second or third grinding step may be discarded.

In another preferred embodiment, the particles of at least one natural material are a part or the whole of said natural material, preferably the whole of said natural material. The method of the present disclosure may be used for any natural material as a whole, or parts thereof. As an example, only parts of a plant may be used, such as the roots, seeds, stems, leaves, fruits, flowers, or the like, depending on the type of natural material.

The Natural Material

The natural material is used in the present disclosure in connection with particles of a natural material, and also in connection with an extract of a natural material. The selection of the natural material for both purposes, i.e. for the particles and for the extract, is independent of each other. Accordingly, in a preferred embodiment of the present disclosure, the natural material of step a1. and the natural material of step a2. are identical. In another preferred embodiment of the present disclosure, the natural material of step a1. and the natural material of step a2. are different. Where in the following specific natural materials which may be used are indicated, these natural materials may be used as the particles or the extract, if not indicated differently.

In another preferred embodiment, the particles of at least one natural material are provided as a mixture of at least two different natural materials independently selected form the natural materials disclosed herein. The method of the present disclosure may be used for any natural material as a whole, or parts thereof. As an example, only parts of a plant may be used, such as the roots.

In another preferred embodiment, the extract of at least one natural material is provided as a mixture of at least two different natural materials independently selected form the natural materials disclosed herein.

In a preferred embodiment, the natural material used for the particles of at least one natural material and/or the extract of natural material is selected from the group consisting of plants, cyanobacteria, algae, and fungi. The plants as used herein may comprise spermatophytina, which may comprise ginkopsida (gingko), gnetopsida, coniferopsida (e.g. needle trees) and angiosperms (flowering plants), which may further comprise the subclasses such as magnoliidae, liliidae (e.g. pineapple), malpighiales (e.g. St. John's wort, willow bark), rosidae (e.g. nettle), brassicales (e.g. carica papaya), fabales (e.g. astragalus), lamiales (e.g. olive tree and olive leaves), dispsacales (e.g. elder). Cyanobacteria may comprise e.g. spirulina. Algae may comprise the domains rhodobionta (e.g. red algae, brown algae and diatoms), green algae and glaucobionta. Fungi may comprise acrasobionta, myxomycota, heterokontobionta, and mycobionta (e.g. pillar fungi like *Agaricus subrufescens*).

In another preferred embodiment, the natural material does not comprise ginseng and/or cellulose fibers. In a further preferred embodiment, the particles of at least one natural material do not comprise ginseng and/or cellulose fibers.

In another preferred embodiment the natural material is selected from the group consisting of gingko, pineapple, St. John's wort, willow bark, nettle, carica papaya, astragalus, olive leaves, elder, spirulina, chlorella algae, red algae, brown algae and diatoms green algae and glaucobionta, agaricus subrufescens, boswellia, rodiola rosea, chincona bark, ipecac, boneset, bryony anil, anil root, curcuma, devil's claw, cat's claw, cystus incanus, flax seed, *Sylibum marianum* (holy thistle), *Chelidonium majus* (celandine), kaplan-pelargonie, echinacea, and grape seeds.

In another preferred embodiment, the nanosuspension comprises a mixture of at least one natural material and the extract of the same or another natural material. As such, the nanosuspension may be a nanosuspension containing a single natural material, or a mixture of more than one natural material, i.e., at least two natural materials. The nanosuspension may as well comprise different parts of the same natural material or extract of a natural material, such as, e.g., parts of the root and parts of the flowers, and/or the nanosuspension may comprise different types of natural materials, such as, e.g., different plants or a plant and a cyanobacteria.

The Dispersing Step

The at least one natural material having a particle size ($D_{100}$) of less than 320 µm provided in step a. is dispersed in a solvent in step b. according to the method of the present disclosure together with the extract of at least one natural material.

In another preferred embodiment, the solvent is water, preferably distilled water, or a mixture of water and ethanol. The water used as solvent may be any kind of water, such as normal water, purified water, distilled water, bi- or tri-distilled water, or demineralized water. Similarly, also the ethanol used may be normal ethanol, or a mixture of water and ethanol. Accordingly, the resulting nanosuspension may be an aqueous nanosuspension, or a nanosuspension in ethanol, or a nanosuspension on the basis of a mixture of water and ethanol, or any other solvent or mixture of solvents. The term "solvent" as used herein refers to a single solvent or a mixture of solvents. Preferably, the solvent is a pharmaceutically acceptable solvent if the nanosuspension is used as a medicament.

In another preferred embodiment, the nanosuspension is an aqueous nanosuspension or a nanosuspension on the basis of a mixture of water and ethanol.

When dispersing the particles of at least one natural material and the extract of at least one natural material in step b. in the solvent, the natural material(s) have a concentration in the range of 0.5 to 20% (w/w), based on the total amount of solvent used, preferably from 2 to 10% (w/w), further preferably from 2 to 5% (w/w) or from 5 to 10% (w/w). In other words, when the particles of at least one natural material are dispersed, the natural materials may have a concentration in the range of 0.5 to 20% (w/w), based on the total amount of solvent used, preferably from 2 to 10% (w/w), further preferably from 2 to 5% (w/w) or from 5 to 10% (w/w), and also the extract of the at least one natural material may be added in step b. in a concentration of from 0.5 to 20% (w/w), based on the total amount of solvent used in the nanosuspension, preferably from 2 to 10% (w/w), further preferably from 2.5 to 5% (w/w) or from 5 to 10% (w/w).

In another preferred embodiment of the present application, the natural material preferably has a concentration in the final nanosuspension in the range of from 0.5 to 70% (w/w), based on the total amount of solvent used, preferably from 40 to 70% (w/w), or from 10 to 40% (w/w). The concentration of the natural material in % (w/w) is based on the total amount of solvent used to prepare the nanosuspension. As an example, with 50 g powder of a natural material (dry particles and dry extract) to 1000 g solvent, 5% (w/w) is prepared. Within the above given concentration range, the further milling of the suspension to a nanosuspension is eased. The particles of at least one natural material and the extract of at least one natural material may have a ratio in the range of 1:10 to 10:1, preferably 1:5 to 5:1, based on the dry mass of the particles and the dry mass of the extract. In particularly preferred embodiments, the ratio is 1:5 or 1:3. Prior to milling, the dispersion may be prepared by stirring the solvent and the natural material together with the extract, e.g., by means of a magnetic stirrer and/or a homogenizer such as Ultra Turrax.

In a particularly preferred embodiment, the total amount of natural material, i.e., the solid matter, present in the nanosuspension at a given concentration results in a solubility factor of above 0.4, or of above 0.5, or of above 0.8, or of above 1, or even of above 1.1.

Further Additives

In another preferred embodiment, the dispersion may additionally contain at least one additive, preferably selected from the group consisting of a mineral (e.g. zinc, magnesium, calcium), a vitamin (e.g. vitamin e, vitamin d, vitamin c), an essential amino acid, a non-essential amino acids, and combinations thereof. The additive may also be termed as supplement. In a further preferred embodiment, the additive is added prior to the milling step c., and/or after the milling step c.

The nanosuspension is stabilized by the use of a stabilizer. In a preferred embodiment, at least one stabilizer is added. In another preferred embodiment, a mixture of stabilizers is added. It is understood that when referring to a stabilizer in the following, also a combination or mixture of stabilizers is comprised. If more than one stabilizer is used, the stabilizers may be added independently of each other, such as at different steps of the method disclosed herein. When adding the stabilizer, it may be added at any point of the method, i.e., prior to the addition of the particles or extract to a solvent in dispersion step b., during dispersion step b., after dispersion step b., during the milling step c., after milling step c., or during or after any optional additional step, such as steps e. and f.

Such stabilizer may be selected from the group consisting of phospholipids, polysorbates, propane-1,2,3-triol (glycerin), electrostatic or steric stabilizers and surfactants. Such stabilizers may be added to the dispersion in step b., or during the milling step c., or even after the milling step c. Some stabilizers are preferably added to the nanosuspension in the dispersion step b., such as phospholipids, nonionic surfactants and emulsifiers, e.g. polysorbate. Other stabilizers are preferably added during the milling step c., like nonionic triblock copolymers, such as poloxamers. Still other stabilizers are preferably added after the milling step c., such as propane-1,2,3-triol or dioctyl sodium sulfosuccinate (DOSS). If a stabilizer is added in dispersion step b., it is preferred to add the stabilizer in an amount of 50% up to 200% (w/w), based on the total amount of natural material, in particular if the stabilizer is a phospholipid. If the stabilizer is a nonionic surfactant or an emulsifier, like polysorbate, it is preferably added in an amount of up to 1.5% (w/w), based on the amount of solvent. During the milling in step c., when specific particle sizes ($D_{90}$) in the range of 2 up to 10 μm have been reached, or if the particle size ($D_{90}$) is not further reduced during milling step c., e.g., by at least 4% during one hour milling time, or if the particle size ($D_{90}$) is increased during milling step c. by at least 10% during one hour milling time, it is preferred to add a stabilizer, like a nonionic triblock copolymer, such as poloxamers.

In a preferred embodiment, the stabilizer is selected from the group consisting of phospholipids; polysorbates; polymers, such as homopolymers, block and graft copolymers (like hydroxypropyl cellulose (HPC), hydroxypropyl methylcellulose (HPMC) and polyvinylpyrrolidone (PVP)); nonionic tri-block copolymers, such as poloxamers (e.g. Kolliphor® P407 or poloxamer 188); copolyvinylpyrrolidone; Labrasol®; Gelucire®; gelatin; lecithin (phosphatides); gum acacia; Locust bean gum; cholesterol; tragacanth; polyoxyethylene alkyl ethers; polyoxyethylene castor oil derivatives; polyoxyethylene sorbitan fatty acid esters; sorbitan fatty acid esters; polyethylene glycols; polyoxyethylene stearates; mono and diglycerides; colloidal silicon dioxide; sodium dodecylsulfate; magnesium aluminum silicate; triethanolamine; stearic acid; calcium stearate; glycerol monostearate; cetostearyl alcohol; cetomacrogol emulsifying wax; short and medium chain alcohols; Labrafil®; Purol-oleique®; propane-1,2,3-triol, polyvinyl alcohol, dioctyl sodium sulfosuccinate (DOSS), and mixtures thereof Preferred examples of polysorbates are polysorbate 80 and polysorbate 20. It is further preferred that the stabilizer is selected from the group consisting of polysorbate 80, polysorbate 20, Kolliphor® P407 and poloxamer 188. In a particularly preferred embodiment, the stabilizer is Kolliphor® P407, or polysorbate 80, such as Tween® 80. In another preferred embodiment, the dispersing step b. comprises the addition of a stabilizer selected from the group consisting of phospholipid and polysorbate.

In another preferred embodiment, the dispersing step b. comprises the addition of a polysorbate in an amount of from 0.5 to 2% (w/w), based on the total amount of the solvent used in the nanosuspension, and/or wherein the polysorbate is selected from the group consisting of polysorbate 80 and polysorbate 20.

In another preferred embodiment, the dispersing step b. comprises the addition of a phospholipid in an amount of from 100% to 200% (w/w), preferably in an amount of 130% to 170% (w/w), based on the amount of the natural material, preferably wherein the phospholipid contains up to 95% (by weight) phosphatidylcholine and from 20 to 30% (by weight) of lysophosphatidylcholine. It is preferred that the phospholipid contains 20-95% phosphatidylcholine, preferably 20-75% phosphatidylcholine, and 20-30% lysophosphatidylcholine (e.g. Lipoid P100, P75, R LPC20 of Lipoid GmbH, Germany). It may also be preferred to add the phospholipid in an amount of from 100 to 300% (w/w), more preferably from 50 to 200% (w/w), based on the total amount of the natural material.

When steric stabilizers are used as stabilizers, the steric stabilizer is adsorbed or attached onto the surface of the nanoparticle and provides a large and dense steric barrier which overcomes attractive Van der Waals forces and hence the steric stabilizer reduces aggregation, agglomeration or even particle fusion. The steric stabilizers are preferably excipients which are pharmaceutically acceptable and may be selected from polymers, such as homopolymers, block and graft copolymers, like hydroxypropyl cellulose (HPC), hydroxypropyl methylcellulose (HPMC) and polyvinylpyrrolidone (PVP). A particularly preferred steric stabilizer is the nonionic tri-block copolymer Kolliphor® P407. Kolliphor® P407 is composed of a central hydrophobic chain of polyoxypropylene (poly(propylene oxide)) flanked by two hydrophilic chains of polyoxyethylene (poly(ethylene oxide)). It may be advantageous to add a steric stabilizer during the milling step c. Thus, it is preferred to add a steric stabilizer in an amount of from 0.5 to 2% (w/w) during the milling step c., further preferably when the particles have a particle size (D90) of less than 5 µm.

Another preferred stabilizer used in the process of the present disclosure is glycerin (propane-1,2,3-triol). Said glycerin is preferably added after milling step c., further preferred in an amount of from 10 to 100% (v/v), amount of from 30 to 100% (v/v) or from 40 to 100% (v/v), even more preferably in an amount of 20% (v/v), 30% (v/v), 40% (v/v) or 50% (v/v), based on the total volume of the solvent.

In addition to glycerin, or in the alternative thereof, dioctyl sodium sulfosuccinate (DOSS) as electrostatic stabilizer may be used, preferably in an amount of from 0.5 to 2% (w/w), based on the total amount of the solvent, and added preferably after milling step c.

In addition to the at least one natural material and the optional oxygen, the nanosuspension of the present disclosure may also comprise at least one compound selected from the group consisting of flavorings, preservatives, surfactants and permeation enhancers, such as riboflavin or ascorbic acid.

It is preferred that a pH buffer is used for stabilizing the nanosuspension and the active agents contained therein. A suitable pH buffer can be selected according to the European Pharmacopoeia 5.0 (publisher: Council of Europe, 5$^{th}$ edition, July 2004, ISBN 9287152810), pages 430 to 435, which are incorporated herein by reference. In a preferred embodiment of the present disclosure, the pH is in the range of from 2.0 to 9.0, preferably from 5.5 to 8.5.

The Milling Step

During milling step c., the dispersion containing the natural material at a particle size of less than 320 µm is milled to a particle size ($D_{90}$) of less than 1000 nm. This may be achieved in any suitable mill.

In a preferred embodiment, said milling step c. is carried out in a wet ball mill, preferably a wet ball agitator mill.

In a further preferred embodiment, said milling step c. comprises a first milling step c.1 in a wet ball mill, preferably a wet ball agitator mill. With a starting particle size ($D_{100}$) of the natural material powder and extract of 40 to 320 µm, said milling step c. comprises a first milling step c.1 in a wet ball mill, preferably a wet ball agitator mill, with a grinding ball diameter from 0.4 to 0.5 mm, and a second milling step c.2 in a wet ball mill, preferably a wet ball agitator mill, with a grinding ball diameter of from 0.1 to 0.2 mm. It is preferred that the first milling step c.1 is used until a particle size ($D_{90}$) of about 2 to 6 µm is reached, and the second milling step c.2 is used until a particle size ($D_{90}$) of about 80 to 500 nm, preferably 80 to 400 nm is reached.

With a starting particle size below 40 µm just one milling step c. in a wet ball mill is used with a grinding ball diameter from 0.1 to 0.2 mm. It is furthermore preferred to have a temperature in the mill chamber of 25 to 36° C., and a rim speed of 10 to 14 m/s, preferably 11 to 14 m/s.

In another preferred embodiment, the milling step c. comprises the addition of a stabilizer, preferably wherein the stabilizer is an electrostatic and/or steric stabilizer, at a particle size $D_{90}<9$ µm preferably $D_{90}<3$ µm, more preferably $D_{90}<800$ nm and most preferably $D_{90}<300$ nm.

Accordingly, in a preferred embodiment, the dispersion of step b. is milled in step c. to a particle size ($D_{100}$) of below 500 nm ($D_{100}<500$ nm), preferably below 300 nm ($D_{100}<300$ nm), further preferably below 250 nm ($D_{100}<250$ nm), and most preferably below 200 nm ($D_{100}<200$ nm), as measured by a dynamic light scattering or laser diffraction analyzer.

The resulting nanosuspension may thus have a particle size ($D_{100}$) of below 500 nm ($D_{100}<500$ nm), preferably below 300 nm ($D_{100}<300$ nm), further preferably below 250 nm ($D_{100}<250$ nm), and most preferably below 200 nm ($D_{100}<200$ nm), as measured by a dynamic light scattering or laser diffraction analyzer, and a particle size of above 40 nm ($D_{100}>40$ nm).

In another preferred embodiment, the dispersion of step b. is milled to a particle size ($D_{100}$) of between 110 nm and 950 nm (110 nm$<D_{100}<$950 nm), preferably between 130 nm and 900 nm (130 nm$<D_{100}<$900 nm), further preferably between 150 nm and 800 nm (150 nm$<D_{100}<$800 nm), and most preferably between 180 nm and 400 nm (180 nm$<D_{100}<$400 nm), as measured by a dynamic light scattering or laser diffraction analyzer.

The resulting nanosuspension may thus have a particle size ($D_{100}$) of between 110 nm and 950 nm (110 nm$<D_{100}<$950 nm), preferably between 130 nm and 900 nm (130 nm$<D_{100}<$900 nm), further preferably between 150 nm and 800 nm (150 nm$<D_{100}<$800 nm), and most preferably between 180 nm and 400 nm (180 nm$<D_{100}<$400 nm), as measured by a dynamic light scattering or laser diffraction analyzer.

During the milling step c., a certain specific energy is applied to the nanosuspension. The specific energy is defined as net energy (gross energy minus idling drive power) of the wet ball agitator mill in [kW] times the milling time in [h] divided by the total amount of the nanosuspension in [t] which is the amount of the solvent, natural material powder and all stabilizers in [t].

The resulting nanosuspension may further be characterized for best stabilization results as a mono-modal suspension, wherein the single mode has an average value of smaller than 300 nm, preferably below 200 nm. Such mono-modal suspension may be achieved by filtering the suspension. The filter may reduce the particle size to a particle size ($D_{90}$) of below 450 nm, preferably below 300 nm, further preferably below 220 nm, or even to a particle size ($D_{100}$) of below 450 nm, preferably below 300 nm, further preferably below 220 nm. As filter device any state of the art device can be used, such as a Sartorius Stedim Biotech filter. If the nanosuspension is filtered to 220 nm, such filtering makes the standard deviation of the particle size distribution even more narrow, which may contribute to the stabilization. In the alternative, a mono-modal suspension may also be achieved by corresponding processing means.

Optional Colloidation

In an alternative to the chemical stabilization using stabilizers as disclosed above, the nanosuspension may also be physically stabilized by means of a colloidator (e.g. modified type Kamena from Levigata GmbH, Germany), as also depicted in FIG. 1. During this process, the nanosuspension is guided within a container (1) by the rotation of rotor (4) and the support rotor (5) into a concave cylinder (3) on its upper end via baffle plates in an almost turbulence free manner. In the interior concave cylinder (3), the descending nanosuspension stream (7) hits the counter rotating upward nanosuspension stream, excited by the rotors (4,5) at the exit at the lower end of the concave cylinder. At the collision of the descending stream of the nanosuspension and the antipodal rotating stream of the nanosuspension, the nanoparticles are statically loaded by friction. This static load or particle charge may cause a separation of the nanoparticles and therefore a physical stabilization. Thereafter, the nanosuspension rises (6) at the exterior hyperbolic cylinder in the reverse direction. The nanosuspension is hereby set in an upward and downward aligned movement. The thermal energy caused hereby is conducted by a water cooler integrated in the double wall (2) of the container (1), where the cooling medium is supplied to and diverted from the double wall (8a, 8b 9a, 9b).

Therefore, in a preferred embodiment, the nanosuspension is further subjected to a colloidation step e. in a colloidator following milling step c., preferably with the addition of oxygen. Such colloidation may furthermore replace the use of stabilizers, and in a further preferred embodiment, the nanosuspension does not contain any stabilizers, in particular it does not contain any propane-1,2,3-triol.

As described in detail above, the nanosuspension of the present disclosure may be chemically or physically stabilized.

The nanosuspension of the present disclosure may additionally contain oxygen ($O_2$). For the present disclosure, if water is enriched with oxygen, the oxygen may be dissolved in water, such as physically or chemically dissolved in the water, or adhere to any of the nanoparticles. In order to enrich the nanosuspension with an extra amount of oxygen, the above described colloidator may be used. In an exemplary method of the present disclosure, about one minute after the start of the colloidation process, oxygen may be added until 20 to 30 mg/liter oxygen is contained in the nanosuspension. By this kind of process, the oxygen is added to the nanosuspension by a so called sucking process in contrast to the pressure method, where oxygen is inserted in a solution via pressure. As oxygen enrichment device, but not necessarily restricted to it, the ultra colloidator of Levigata Ltd. may be used.

In a preferred embodiment of the present disclosure, the nanosuspension has an oxygen concentration of from 20 to 30 mg/l.

The resulting nanosuspension may have a zeta potential between −10 mV and +10 mV, more preferably between −20 mV and +20 mV, and more preferably between −40 mV and +40 mV measured with a zeta sizer (Malvern instruments, Germany).

The nanosuspension may optionally be filtered in a filtering step after step c. and optionally prior to or after step e. With such filtering, the size of the nanoparticles in the nanosuspension may further be adapted to the need. As an example, the sterile filtering of the nanosuspension may be mentioned. Such sterile filter may reduce the particle size to a particle size ($D_{90}$) to below 450 nm, preferably below 220 nm. As filter device any state of the art device can be used, such as a standard Millipore filter. If the nanosuspension is filtered to 220 nm, such filtering makes the standard deviation of the particle size distribution even more narrow, which may contribute to the stabilization.

In a preferred embodiment of the present disclosure, the nanosuspension is filtered after step c. and optionally prior to or after step e., preferably with a sterile filter, further preferably to a particle size below 450 nm, and more preferably below 220 nm.

Prior to use of the nanosuspension, the concentration of the nanosuspension may be adapted according to the needs. On the one hand, the nanosuspension may be diluted by the addition of further solvent. On the other hand, the concentration of the nanosuspension may be increased in a further step f. The increase of concentration may be achieved by evaporation of solvent, preferably in a drying chamber, further preferably at a temperature not exceeding 40° C., and optionally at reduced pressure. The final nanosuspension then preferably has a concentration of natural material in the range of from 10 to 40% (w/w), preferably of from 10 to 20% (w/w), based on the total amount of solvent present in the nanosuspension.

Therefore, in a preferred embodiment, the concentration of the nanosuspension is increased in a further step f. by evaporation of solvent, preferably in a drying chamber, to a concentration of the natural material of 10 to 40% (w/w), preferably to 10 to 20% (w/w), based on the total amount of solvent present in the nanosuspension.

Nanosuspension and Use Thereof

The above described method for the preparation of a nanosuspension results in a nanosuspension. Accordingly, the present disclosure also relates to a nanosuspension obtainable according to any one of the methods described herein.

Furthermore, the nanosuspension of the present disclosure may be used in the preparation of a medicament or supplement, such as a food supplement.

The nanosuspension of the present disclosure may advantageously be used in the preparation of a medicament for buccal, topical and/or oral application to an animal, preferably a human.

Nanosuspensions of natural materials offer distinct advantages including the possibility to be administered via the trans-mucosal route. The nanosuspensions of natural materials contain a higher concentration of active agents per volume unit, smaller particles of non-water soluble active agents and provide therefore new possibilities for immune-modulating drugs, where immune-modulating active agents are taken-up by immune cells, which require small particle size of the immune-modulating active agents. Furthermore, it is believed that the milling of the natural material to a particle size of below 1 μm also helps to liberate the active agents so that a higher concentration of active agents contained in the natural material are available, or that such active agents are made available at all.

The mucosal adsorption of an active agent can be increased by a reduced particle size due to improved solubility. In case of aggregation the bioavailability of the drug is decreased. Therefore it is advantageous to provide a nanosuspension having a high stability over a prolonged period of time. Useful stabilizers are, for example, electrostatic, steric and physical stabilizer. If the particle size of active agents are below 400 nm, they can be better absorbed at the point of action in the human organism. Further, if the particle size of secondary plant compounds are below 400 nm, they can better stabilize the active agent and support them in its overall effectiveness.

For oral cavity administration, the drug should preferably be liquid and efficacious in low dosages since the uptake capacity of substances via the oral cavity is limited. Furthermore the particles of a drug administered via the oral cavity should be in the nanometer range, e.g., less than approx. 300-400 nm, otherwise the passage through the oral cavity is limited. Since the nanosuspension of the present disclosure may be provided with a particle size $D_{100}$ below 400 nm, the nanosuspension may advantageously be used for oral cavity administration.

The nanosuspensions of the present disclosure may be used in the treatment or prevention of cancer, inflammatory bowel disease (IBD), arthritis, human immunodeficiency virus (HIV), other viral diseases, dermatological diseases, such as neurodermatitis or psoriasis, or auto-immune diseases, such as multiple sclerosis, vasculitis, rheumatoid arthritis or dermatomyositis.

The nanosuspensions of the present disclosure are effective in providing higher concentrations of the active agents of natural materials in the bloodstream over a longer period of time as compared to e.g. extracts prepared from the natural materials. This especially applies to hydrophobic compounds contained in such natural materials. Furthermore, nanosuspensions containing immune-modulatory compounds from natural materials stimulate the immune system in a broader and more intense manner, since they contain more immune stimulating particles in the nanometer range and higher amount, which are better taken up or recognized by the respective immune subpopulation compared to, e.g., extracts.

EXPERIMENTAL SECTION

In the following, the present invention is illustrated in more detail by way of Examples. However, it is understood that the scope of protection is only determined by the attached claims, not being restricted to any of the following Examples. The following Examples are set forth to assist in understanding the invention and should not be construed as specifically limiting the invention described and claimed herein. Such variations of the invention, including the substitution of all equivalents now known or later developed, that would be within the purview of those skilled in the art, and changes in formulation or changes in experimental design, are to be considered to fall within the scope of the invention incorporated herein.

Example 1

Figure 2:
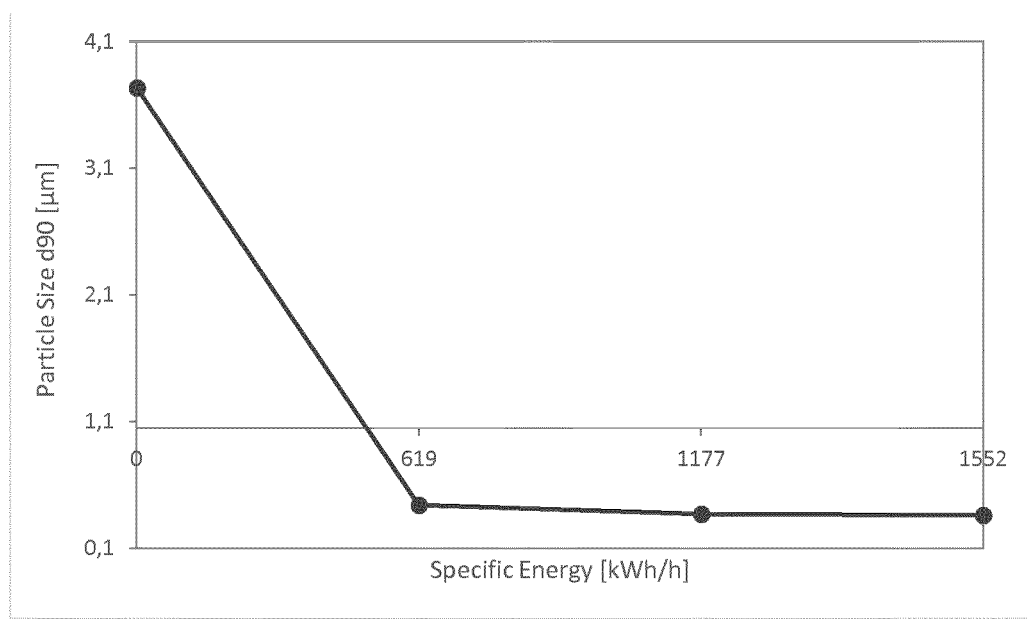
FIG. 2: is a graph showing the particle size $D_{90}$ [µm] depending on the input of specific energy [kWh/t] during wet milling of Example 1.

Formulation of a 3% *Curcuma longa* and Curcumin Nanosuspension 20 g *Curcuma longa* powder (particle size $D_{100}$: <320 µm), and 100 g dry curcumin extract (Alfa Aesar GmbH & Co KG) (ratio of 1:5 (w/w)), 300 g Lipoid P100 (Lipoid GmbH, Germany, 7.5% (w/w)), 60 g polysorbate Tween® 80 (AppliChem GmbH, Germany, 1.5% (w/w)) and 60 g dioctyl sodium sulfosuccinate (Alfa Aesar, GmbH & Co KG, Germany, 1.5% (w/w)) were homogenized in 1500 g bi-distilled water by Ultra Turrax (T 18 digital, IKA-Werke GmbH & CO. KG, Germany). Before milling, bi-distilled water is added to the dispersion to result in a total mass of 4000 g. The resulting dispersion was milled in a wet ball agitator mill (type X1, Buehler AG, Switzerland) using yttrium stabilized zirconia balls of size 0.1 to 0.2 mm. The amount of specific energy [kWh/t] used for the milling can be seen from FIG. 2. The particle size ($D_{90}$) of the nanosuspension was reduced to 308 nm at a specific energy of 1552 kWh/t (see also FIG. 2).

Example 2

Figure 3:
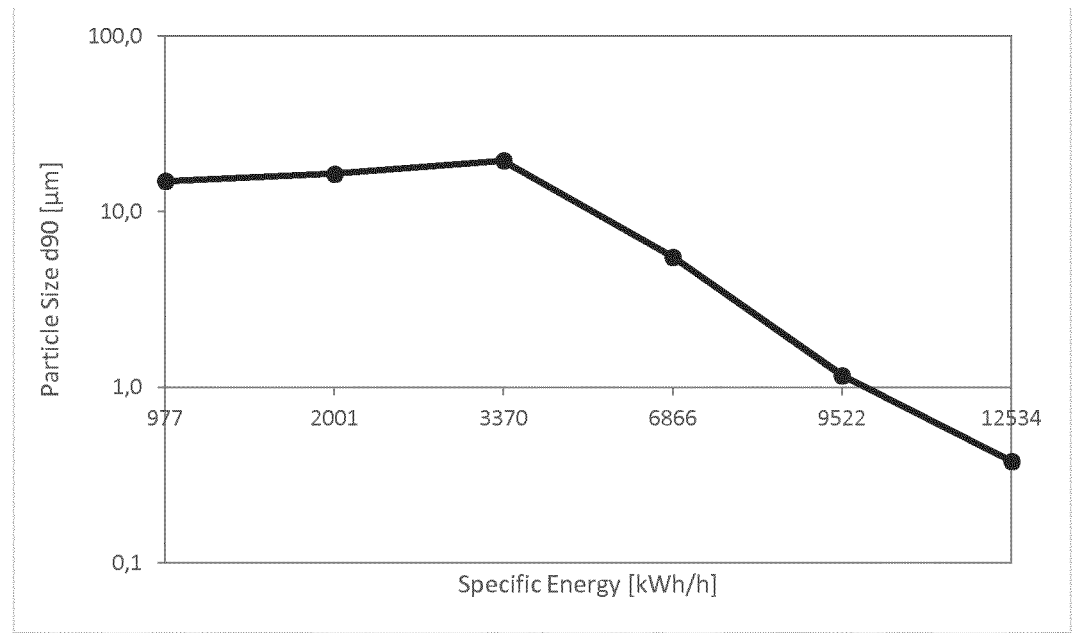
FIG. 3: is a graph showing the particle size $D_{90}$ [µm] depending on the input of specific energy [kWh/t] during wet milling of Example 2.
Figure 4:
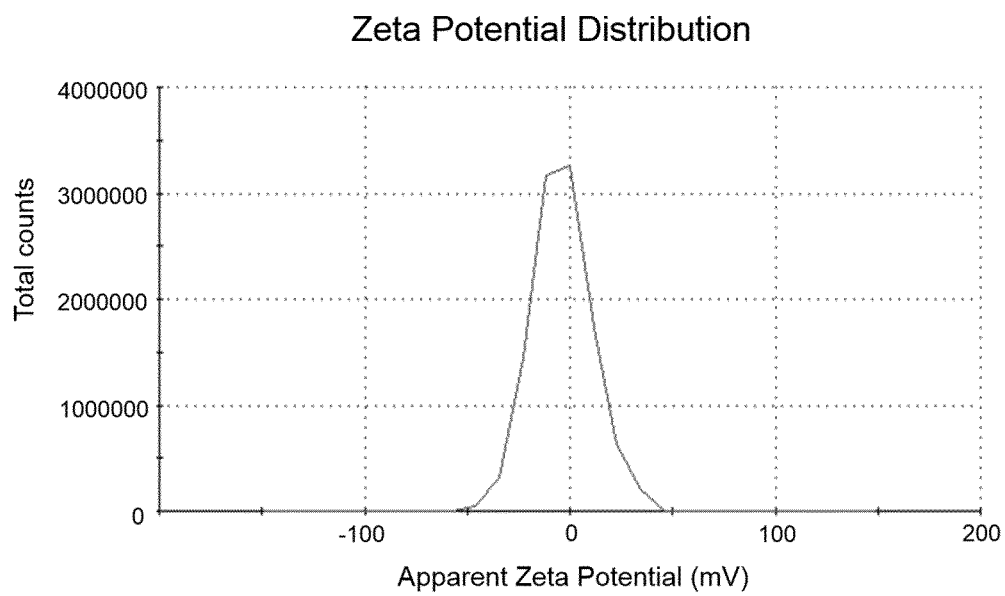
FIG. 4: shows the distribution of the zeta potential of the nanosuspension according to Example 2.

Formulation of a 5% *Curcuma longa* and Curcumin Nanosuspension 33 g *Curcuma longa* powder (particle size $D_{100}$: <320 µm), and 167 g dry curcumin extract (Alfa Aesar GmbH & Co KG) (ratio of 1:5 (w/w)), 300 g Lipoid P100 (Lipoid GmbH, Germany, 7.5% (w/w)) and 60 g dioctyl sodium sulfosuccinate (Alfa Aesar, GmbH & Co KG, Germany, 1.5% (w/w)) were homogenized in 1500 g bi-distilled water by Ultra Turrax (T 18 digital, IKA-Werke GmbH & CO. KG, Germany). Before milling, bi-distilled water is added to the dispersion to result in a total mass of 4000 g. The dispersion was milled in a wet ball agitator mill (type X1, Buehler AG, Switzerland) using yttrium stabilized zirconia balls of size 0.4 to 0.5 mm. By reaching a particle size of about 25 µm with a specific energy [kWh/t] of about 2900, the milling balls were changed to a size of 0.1 to 0.2 mm. The particle size ($D_{90}$) of the nanosuspension was reduced to 380 nm at a specific energy of 12534 kWh/t while adding 60 g Kolliphor® P 188 (1.5% (w/w)) during the milling (see also FIG. 3). The nanosuspension is stabilized with steric excipients using Kolliphor® P 188 and electrostatic excipients using dioctyl sodium sulfosuccinate. Depending on the zeta potential (measured with zeta sizer, Malvern instruments, Germany), the nanosuspension is mainly stabilized via steric compounds (see also FIG. 4).

Example 3

Comparison of Solubility of Curcuminoids in Water

The solubility of an active agent with low solubility in water can be highly increased in the nanosuspension. The solubility of curcuminoid is about 0.1 mg/ml in water. An aqueous extract was prepared using 300 mg dry powder composed of 50 mg *Curcuma longa* powder (particle size $D_{100}$<320 µm) and 250 mg dry curcumin extract (Alfa Aesar GmbH & Co KG; particle size of $D_{100}$<40 µm). The combined dry powder was suspended in 10 ml distilled water, resulting in a concentration of 3% (w/w). The suspension was incubated at 25° C. for 2 h and then centrifuged with 8000×g for 10 min. The content of curcuminoids in the supernatant was measured using LC/MS system (Nexera XR, Shimadzu; Triple Quad 4500, AB Sciex) and resulted in a content of about 0.1 mg/ml.

Figure 5:
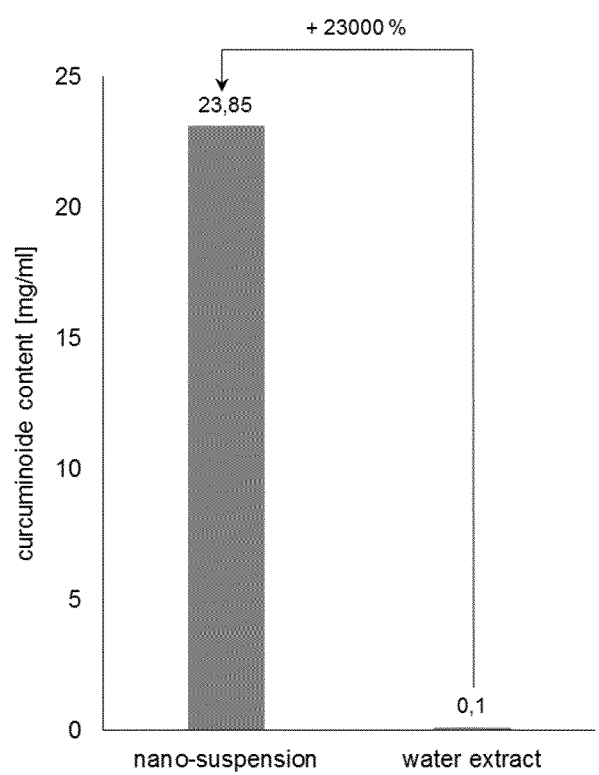
FIG. 5: shows the content of an active agent with low solubility in water [mg/ml] and the increased solubility of the substance in the nanosuspension according to Example 3.

In contrast thereto, the solubility of the nanosuspension (3% (w/w) as prepared in Example 1) is 23.1 mg/ml. The prepared nanosuspension shows increased solubility of 23000% of free curcuminoid compared to the above water extract with the same concentration of *Curcuma longa* powder and curcumin extract (see also FIG. 5).

Embodiments

The present disclosure also pertains to the following numbered embodiments.
1. A method for the preparation of a nanosuspension comprising nanoparticles of at least one natural material and an extract of at least one natural material, wherein the method comprises the steps of
   a1. Providing particles of at least one natural material having a particle size ($D_{100}$) of less than 320 µm;
   a2. Providing an extract of at least one natural material;
   b. Dispersing said particles of at least one natural material of step a1. and said extract of at least one natural material of step a2. in a solvent;
   c. Milling the dispersion of step b. to a particle size ($D_{90}$) of below 1000 nm ($D_{90}$<1000 nm); and
   d. Adding a stabilizer.
2. The method according to embodiment 1, wherein the at least one natural material of step a1. and the at least one natural material of step a2. are identical.
3. The method according to any one of the preceding embodiments, wherein the at least one natural material is, independently, selected from the group consisting of plants, cyanobacteria, algae and fungi, and/or wherein the natural material does not comprise ginseng and/or cellulose fibers.
4. The method according to any one of the preceding embodiments, wherein the at least one natural material is a part or the whole of said natural material, preferably the whole of said natural material.
5. The method according to any one of the preceding embodiments, wherein the nanosuspension comprises a mixture of nanoparticles of at least two natural materials and/or a mixture of extracts of at least two natural materials.
6. The method according to any one of the preceding embodiments, wherein the natural material is dried in a step a1.1, prior to step a1., preferably lyophilized and/or thermally dried.
7. The method according to any one of the preceding embodiments, wherein extract of the at least one natural material is dried in a step a2.1, prior to step a2., preferably lyophilized and/or thermally dried.
8. The method according to any one of the preceding embodiments, wherein the natural material provided in step a1. has a water content w of below 15% (w<15%), preferably below 12% (w<12%), more preferably below 10% (w<10%), and most preferably below 8% (w<8%).
9. The method according to any one of the preceding embodiments, wherein the natural material is pre-ground prior to and/or after the drying in step a1.1, preferably in a knife mill, and optionally sieved to a particle size ($D_{100}$) of less than 320 µm.
10. The method according to any one of the preceding embodiments, wherein the extract of the at least one natural material is selected from a dry powder, a soft extract, and a liquid extract, and preferably selected from a dry powder, an aqueous extract, and an alcoholic extract.
11. The method according to any one of the preceding embodiments, wherein the solvent is water, preferably distilled water, or a mixture of water and ethanol.
12. The method according to any one of the preceding embodiments, wherein the nanosuspension is an aqueous nanosuspension or a nanosuspension on the basis of a mixture of water and ethanol.
13. The method according to any one of the preceding embodiments, wherein the at least one natural material is dispersed in step b. in a concentration of from 0.5 to 20% (w/w), based on the total amount of solvent used in the nanosuspension, preferably from 2 to 10% (w/w), further preferably from 2 to 5% (w/w) or from 5 to 10% (w/w).
14. The method according to any one of the preceding embodiments, wherein the extract of the at least one natural material is added in step b. in a concentration of from 0.5 to 20% (w/w), based on the total amount of solvent used in the nanosuspension, preferably from 2 to 10% (w/w), further preferably from 2.5 to 5% (w/w) or from 5 to 10% (w/w).
15. The method according to any one of the preceding embodiments, wherein the dispersing step b. or the milling step c. comprises the addition of the stabilizer, preferably wherein the dispersing step b. comprises the addition of a phospholipid and/or polysorbate.
16. The method according to embodiment 15, wherein the dispersing step b. comprises the addition of a polysorbate in an amount of from 0.5 to 2% (w/w), and/or wherein the polysorbate is selected from the group consisting of polysorbate 80 and polysorbate 20.
17. The method according to embodiment 15, wherein the dispersing step b. comprises the addition of a phospholipid in an amount of from 50 to 200% (w/w), based on the total amount of the natural material, preferably wherein the phospholipid contains up to 95% (by weight) phosphatidylcholine and/or from 20 to 30% (by weight) of lysophosphatidylcholine.
18. The method according to any one of the preceding embodiments, wherein the milling of step c. is carried out in a wet ball agitator mill.
19. The method according to embodiment 18, wherein milling step c. comprises a first milling step c.1 in a wet ball mill, preferably a wet ball agitator mill, with a grinding ball diameter of from 0.4 to 0.5 mm, and a second milling step c.2 in a wet ball mill, preferably a wet ball agitator mill, with a grinding ball diameter of from 0.1 to 0.2 mm.
20. The method according to any one of the preceding embodiments, wherein milling step c. comprises the addition of the stabilizer, preferably wherein the stabilizer is an electrostatic and/or steric stabilizer, at a particle size $D_{90}$<9 µm preferably $D_{90}$<3 µm, more preferably $D_{90}$<800 nm and most preferably $D_{90}$<300 nm.
21. The method according to any one of the preceding embodiments, wherein the stabilizer is selected from the group consisting of phospholipids; polysorbates; polymers, such as homopolymers, block and graft copolymers (like hydroxypropyl cellulose (HPC), hydroxypropyl methylcellulose (HPMC) and polyvinylpyrrolidone (PVP)); nonionic tri-block copolymers, such as poloxamers (e.g. Kolliphor® P407 or poloxamer 188); ionic polymers such as polyacrylic acid (PAA) and chitosan; copolyvinylpyrrolidone; Labrasol®; Gelucire®; gelatin; lecithin (phosphatides); gum acacia; Locust bean gum; cholesterol; tragacanth; polyoxyethylene alkyl ethers; polyoxyethylene castor oil derivatives; polyoxyethylene sorbitan fatty acid esters; sorbitan fatty acid esters; polyethylene glycols; polyoxyethylene stearates; mono and diglycerides; colloidal silicon dioxide; sodium dodecylsulfate; magnesium aluminum silicate; triethanolamine; stearic acid; calcium stearate; glycerol monostearate; cetostearyl alcohol; cetomacrogol emulsifying wax; short and medium chain alcohols; Labrafil®; Purol-oleique®; propane-1,2,3-triol, polyvinyl alcohol, dioctyl sodium sulfosuccinate (DOSS), and mixtures thereof, preferably wherein the stabilizer is selected from the group consisting of polysorbate 80, polysorbate 20, Kolliphor® P407 and poloxamer 188.

22. The method according to any one of the preceding embodiments, wherein the method comprises the addition of propane-1,2,3-triol (glycerin) after milling step c. was finished.

23. The method according to embodiment 22, wherein the stabilizer is glycerin in an amount of 10 to 100% (v/v), preferably from 30 to 100% (v/v), further preferably in an amount of 20% (v/v), 30% (v/v), 40% (v/v) or 50% (v/v), based on the total volume of the solvent.

24. Method according to any one of the preceding embodiments, wherein the nanosuspension is further subjected to a colloidation step e. in a colloidator following milling step c., preferably with the addition of oxygen, where the nanosuspension not necessarily contains propane-1,2,3-triol.

25. The method according to embodiment 24, wherein the nanosuspension has an oxygen concentration of 20 to 30 mg/l.

26. Method according to any one of the preceding embodiments, wherein the nanosuspension is filtered after step c. and optionally prior to or after step e., preferably with a sterile filter, further preferably to a particle size below 450 nm, and more preferably below 220 nm.

27. Method according to any one of the preceding embodiments, wherein the nanosuspension additionally comprises at least one compound selected from the group consisting of flavorings, preservatives, surfactants and permeation enhancers.

28. Method according to any one of the preceding embodiments, wherein the dispersion of step b. is milled to a particle size ($D_{100}$) of below 500 nm ($D_{100}$<500 nm), preferably below 300 nm ($D_{100}$<300 nm), further preferably below 250 nm ($D_{100}$<250 nm), and most preferably below 200 nm ($D_{100}$<200 nm), as measured by a dynamic light scattering or laser diffraction analyzer.

29. Method according to any one of the preceding embodiments, wherein the dispersion of step b. is milled to a particle size ($D_{100}$) of between 110 nm and 950 nm (110 nm<$D_{100}$<950 nm), preferably between 130 nm and 900 nm (130 nm<$D_{100}$<900 nm), further preferably between 150 nm and 800 nm (150 nm<$D_{100}$<800 nm), and most preferably between 180 nm and 400 nm (100 nm<$D_{100}$<400 nm), as measured by a dynamic light scattering or laser diffraction analyzer.

30. Method according to any one of the preceding embodiments, wherein the concentration of the nanosuspension is increased in a further step f. by evaporation of solvent, preferably in a drying chamber, to a concentration of the natural material of 10 to 40% (w/w), preferably to 10 to 20% (w/w), based on the total volume of the nanosuspension.

31. Method according to any one of the preceding embodiments, wherein the at least one natural material is present in the nanosuspension at a concentration resulting in a solubility factor of more than 0.4, or of more than 0.5, or of more than 0.8, or of more than 1, or even of more than 1.1.

32. Method according to any one of the preceding embodiments, wherein the method comprises the addition of at least one additive, preferably selected from the group consisting of a mineral, a vitamin, an essential amino acid, a non-essential amino acids, and combinations thereof.

33. Nanosuspension obtainable according to a method of any one of the previous embodiments.

34. Nanosuspension according to embodiment 33 for use in the preparation of a medicament, or a supplement, preferably a food supplement.

35. Nanosuspension according to embodiment 33 for use in the preparation of a medicament for buccal, topical or oral application to an animal, preferably a human.

36. Nanosuspension according to embodiment 33 for use in the preparation of a medicament for parenteral, intrathecal, intravenous, transdermal, or trans mucosal application, preferably buccal, topical or oral application, to an animal, preferably a human.

37. Nanosuspension according to embodiment 33 for use in the treatment or prevention of cancer, inflammatory bowel disease (IBD), arthritis, human immunodeficiency virus (HIV), other viral diseases, dermatological diseases, such as neurodermatitis or psoriasis, or auto-immune diseases, such as multiple sclerosis, vasculitis, rheumatoid arthritis or dermatomyositis.

38. Use of a nanosuspension according to embodiment 33 for the preparation of a medicament.

39. Use of a nanosuspension according to embodiment 33 for the preparation of a medicament for the treatment or prevention of cancer, inflammatory bowel disease (IBD), arthritis, human immunodeficiency virus (HIV), other viral diseases, dermatological diseases, such as neurodermatitis or psoriasis, or auto-immune diseases, such as multiple sclerosis.

40. Method for the treatment or prevention of cancer, inflammatory bowel disease (IBD), arthritis, human immunodeficiency virus (HIV), other viral diseases, dermatological diseases, such as neurodermatitis or psoriasis, or auto-immune diseases, such as multiple sclerosis comprising administering an effective amount of a nanosuspension according to embodiment 33 to a patient in need thereof.

The invention claimed is:

1. A method for the preparation of a nanosuspension comprising nanoparticles of at least one natural material and an extract of at least one natural material, wherein the method comprises:
    dispersing, in a solvent:
        (1) particles of at least one natural material having a particle size ($D_{100}$) of less than 320 μm, which are not particles of an extract, and
        (2) an extract of at least one natural material,
    thereby obtaining a dispersion;
    milling the dispersion to a particle size ($D_{90}$) of below 1000 nm; and
    adding a stabilizer,
    wherein the natural material does not comprise ginseng, and
    wherein, prior to the dispersing, the particles of the at least one natural material (1) comprise an active agent, in approximately the same concentration as in the natural source of the particles of the at least one natural material.

2. The method of claim 1, wherein the nanosuspension comprises a mixture of nanoparticles of at least two natural materials and/or a mixture of extracts of at least two natural materials.

3. The method of claim 1, wherein the natural material prior to the dispersing has a water content w of below 15%.

4. The method of claim 1, wherein the solvent is water or a mixture of water and ethanol.

5. The method of claim 1, wherein the dispersing or the milling comprises the addition of the stabilizer.

6. The method of claim 1, wherein the milling is carried out in a wet ball agitator mill.

7. The method according to claim 6, wherein milling comprises a first milling in a wet ball mill with a grinding ball diameter of from 0.4 to 0.5 mm, and a second milling in a wet ball mill with a grinding ball diameter of from 0.05 to 0.2 mm.

8. The method of claim 1, wherein the stabilizer is selected from the group consisting of phospholipids; polysorbates; polymers; nonionic tri-block copolymers; copolyvinylpyrrolidone; caprylocaproyl polyoxyl-8 glycerides NE; lauroyl polyoxyl-32 glycerides NF; gelatin; lecithin (phosphatides); gum acacia; Locust bean gum; cholesterol; tragacanth; polyoxyethylene alkyl ethers; polyoxyethylene castor oil derivatives; polyoxyethylene sorbitan fatty acid esters; sorbitan fatty acid esters; polyethylene glycols; polyoxyethylene stearates; mono and diglycerides; colloidal silicon dioxide; sodium dodecylsulfate; magnesium aluminum silicate; triethanolamine; stearic acid; calcium stearate; glycerol monostearate; cetostearyl alcohol; cetomacrogol emulsifying wax; short and medium chain alcohols; oleoyl polyoxyl-6 glycerides NF; polyglycerol oleate; propane-1,2,3-triol; polyvinyl alcohol; dioctyl sodium sulfosuccinate (DOSS); and mixtures thereof.

9. The method of claim 1, wherein the nanosuspension is filtered after the milling and optionally prior to or after colloidation.

10. The method of claim 1, wherein the dispersion is milled to a particle size ($D_{100}$) of below 500 nm, as measured by a dynamic light scattering or laser diffraction analyzer.

11. The method of claim 1, wherein the at least one natural material is present in the nanosuspension at a concentration resulting in a solubility factor of more than 0.4.

12. The method of claim 1, wherein the at least one natural material has a greater solubility in water after milling the dispersion and adding the stabilizer than the at least one natural material had before the milling.

13. The method of claim 1, wherein the at least one natural material is present in the nanosuspension at a concentration resulting in a solubility factor of more than 1.

14. The method of claim 1, wherein the extract is an extract of a natural material which is the same material as the at least one natural material having a particle size (D100) of less than 320 μm.

15. The method of claim 14, wherein the extract is curcumin extract and the at least one natural material having a particle size (D100) of less than 320 μm is *Curcuma longa* powder.

16. The method of claim 1, wherein the dispersion is milled to a particle size ($D_{90}$) of below 400 nm.

17. The method of claim 1, wherein the particles of at least one natural material having a particle size ($D_{100}$) of less than 320 μm are particles of at least one selected from the group consisting of plants, cyanobacteria, algae, and fungi.

18. The method of claim 1, wherein the particles of at least one natural material having a particle size ($D_{100}$) of less than 320 μm are particles of the whole of the natural material, or are particles of a part of the natural material.

19. The method of claim 18, wherein the particles of at least one natural material having a particle size ($D_{100}$) of less than 320 μm are particles of at least one part of the natural material selected from the group consisting of roots, seeds, stems, leaves, fruits, and flowers.

* * * * *